(12) United States Patent
Davey et al.

(10) Patent No.: US 7,527,939 B2
(45) Date of Patent: May 5, 2009

(54) POLYCLONAL-MONOCLONAL ELISA ASSAY FOR DETECTING N-TERMINUS PROBNP

(75) Inventors: Michelle Davey, Brampton (CA); George Jackowski, Kettleby (CA); Peter Kupchak, Toronto (CA); Eric Stanton, Burlington (CA)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 11/375,432

(22) Filed: Mar. 13, 2006

(65) Prior Publication Data

US 2006/0154321 A1    Jul. 13, 2006

Related U.S. Application Data

(63) Continuation of application No. 10/359,051, filed on Feb. 4, 2003, now abandoned, which is a continuation of application No. 10/300,733, filed on Nov. 18, 2002, now abandoned.

(51) Int. Cl.
| | |
|---|---|
| C07K 16/26 | (2006.01) |
| C12P 21/08 | (2006.01) |
| C12Q 1/28 | (2006.01) |
| G01N 33/53 | (2006.01) |
| G01N 33/535 | (2006.01) |
| G01N 33/543 | (2006.01) |
| G01N 33/577 | (2006.01) |
| G01N 33/74 | (2006.01) |
| C12N 5/20 | (2006.01) |
| G01N 33/544 | (2006.01) |
| G01N 33/545 | (2006.01) |

(52) U.S. Cl. ............... 435/7.94; 435/7.1; 435/7.5; 435/7.92; 435/28; 435/70.21; 435/452; 435/336; 436/518; 436/528; 436/531; 436/547; 436/548; 436/811; 530/388.24; 530/389.2; 530/391.1; 530/413; 530/800

(58) Field of Classification Search ............ 435/7.1, 435/7.92, 7.94, 7.95, 70.21, 452, 336, 7.5, 435/28; 436/518, 528, 531, 547, 548, 811; 530/324, 350, 388.24, 389.2, 391.1, 413, 530/800

See application file for complete search history.

(56) References Cited

U.S. PATENT DOCUMENTS

| | | | |
|---|---|---|---|
| 5,786,163 A | 7/1998 | Hall | |
| 6,117,644 A | 9/2000 | DeBold | 435/7.1 |
| 6,960,472 B2 * | 11/2005 | DeBold | 435/336 |

FOREIGN PATENT DOCUMENTS

| | | | |
|---|---|---|---|
| AU | 758562 | * | 8/2000 |
| WO | WO89/12069 | | 12/1989 |
| WO | WO00/35951 | | 6/2000 |
| WO | WO00/45176 | | 8/2000 |

OTHER PUBLICATIONS

Karl et al., 1999. Development of a novel, N-terminal-pro-BNP (NT-proBNP) assay with a low detection limit. Scand. J. Clin. Lab. Invest. 59(Suppl. 230): 177-181.*

Sudoh et al, "Cloning and sequence analysis of cDNA encoding a precursor for human brain natriuretic peptide", Biochemical and Biophysical Research Communications, 159(3):1427-1434 (1989).

Hunt et al, "Immunoreactive amino-terminal pro-brain natriuretic peptide (NT-PROBNP): a new marker of cardiac impairment", Clinical Endocrinology, 47:287-296 (1997).

Clerico, et al. "Measurement of Cardiac Natriuretic Hormones (Atrial Natriuretic Peptide, Brain Natriuretic Peptide, and Related Peptides) in Clinical Practice: The Need for a New Generation of Immunoassay Methods", Clinical Chemistry 46 (10):1529-1534 (2000).

Fischer, et al. "Evaluation of a New, Rapid Bedside Test for Quantitative Determination of B-Type Natriuretic Peptide", Clinical Chemistry, 47 (3): 591-594 (2001).

* cited by examiner

*Primary Examiner*—Ann Y Lam
*Assistant Examiner*—James L Grun
(74) *Attorney, Agent, or Firm*—Mintz Levin Cohn Ferris Glovsky & Popeo P.C.

(57) ABSTRACT

A specific and sensitive in vitro ELISA assay and diagnostic test kit is disclosed for determining levels of NT-proBNP protein in a variety of bodily fluids, non-limiting examples of which are blood, serum, plasma, urine and the like. The NT-proBNP ELISA assay test employs the sandwich ELISA technique to measure circulating NT-proBNP in human plasma. In order to obtain antibodies with specific binding properties for targeted amino acid sequences within human proBNP, recombinant human proBNP (or rhproBNP) was expressed and purified for use as an immunogen. Polyclonal antibodies (PAb) to specific amino acid sequences were subsequently purified from goat serum by sequential affinity purification. Monoclonal antibodies were raised against specific polypeptides. Recombinant human NT-proBNP (or rhNT-proBNP) was expressed and purified in order to obtain material for use in calibration of a quantitative method for measurement of human NT-proBNP.

4 Claims, 4 Drawing Sheets

FIGURE 1

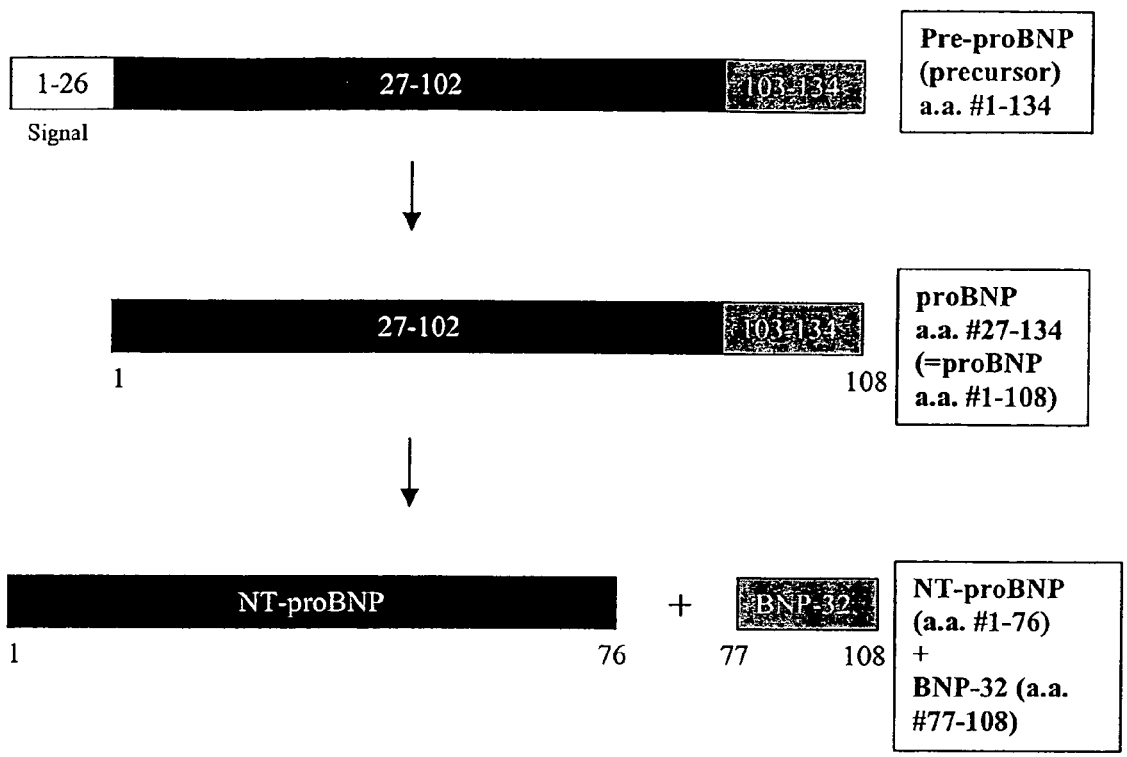

Synthesized proBNP amino acid peptides (used for goat PAb affinity purification):

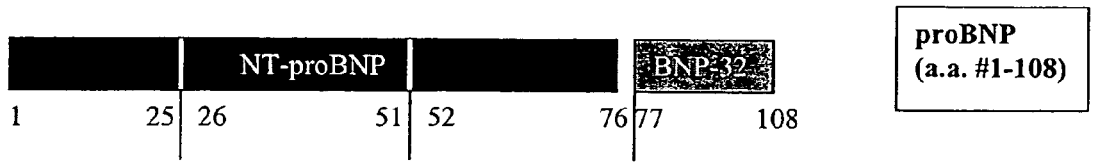

Peptide 1 = proBNP a.a. #1-25
Peptide 2 = proBNP a.a. #26-51
Peptide 3 = proBNP a.a. #52-76

Note: Goat polyclonal antibody affinity purified against amino acid peptide 2 (a.a. 26-51) was selected for use as capture. Goat polyclonal antibody affinity purified against amino acid peptide 1 (a.a. 1-25) was selected for use as detector. Goat polyclonal antibody was also affinity purified against amino acid peptide 3 (a.a. 52-76), however this material was not selected for use in the final NT-proBNP ELISA format.

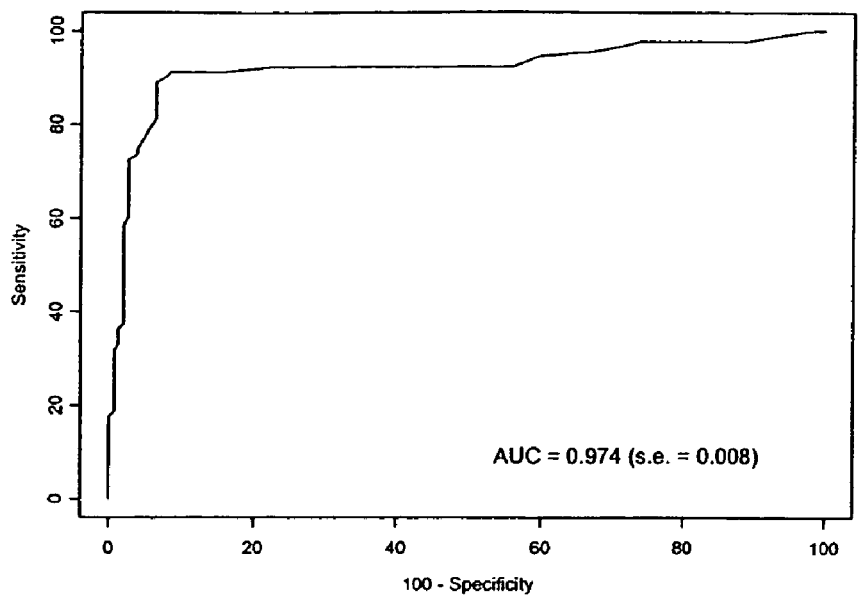
*Figure 2: ROC curve for NT-proBNP (goat-6G11 assay).*
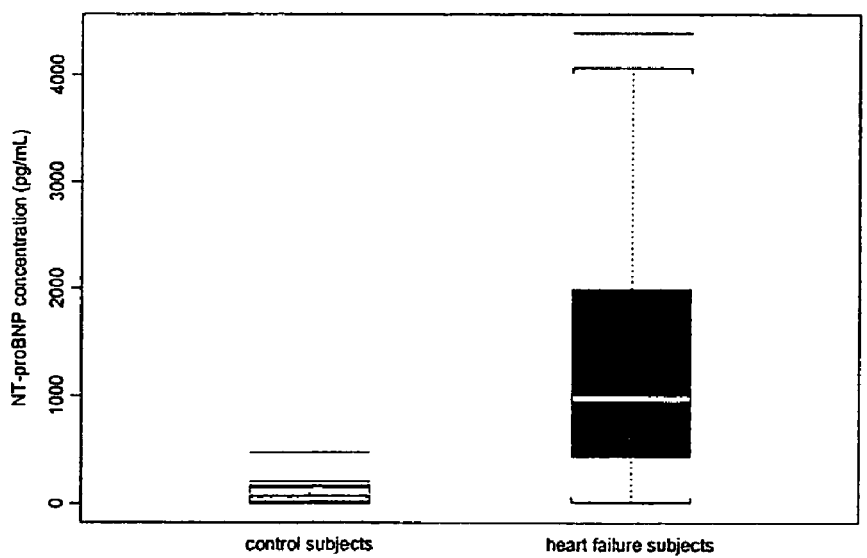
*Figure 3: NT-proBNP (goat-6G11 assay) levels in control subjects and heart failure (NYHA Class III and IV) subjects.*

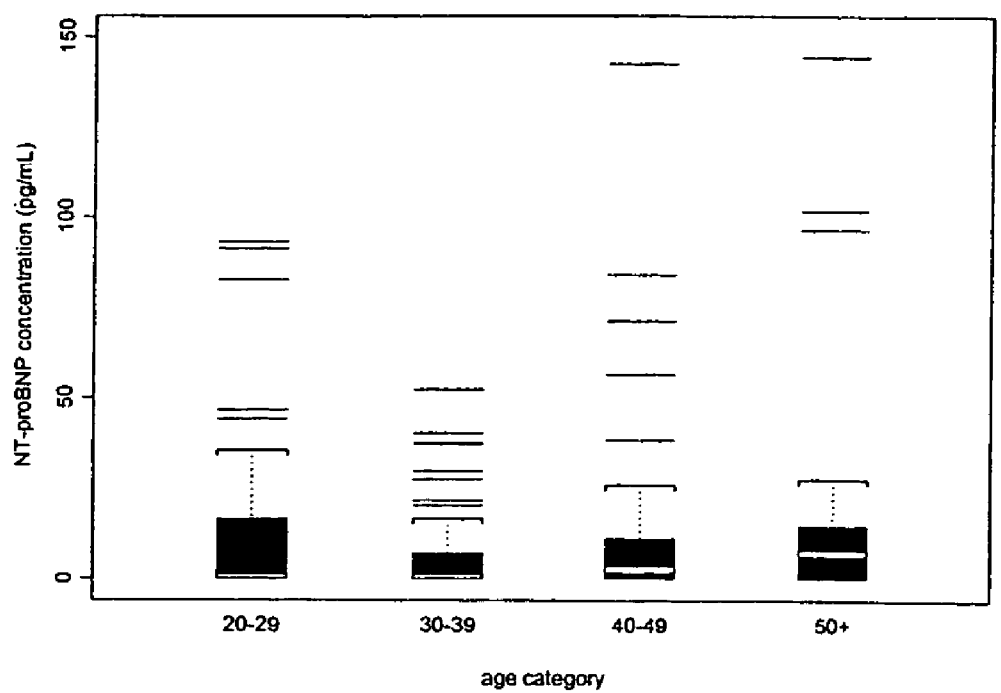
*Figure 4: NT-proBNP levels in control subjects, stratified by age category.*

NT-proBNP ELISA Procedure (Goat/6G11 Assay Format)

SEQUENCE LISTING

```
<160> NUMBER OF SEQ ID NOS: 1

<210> SEQ ID NO 1
<211> LENGTH: 108
<212> TYPE: PRT
<213> ORGANISM: Homo sapiens

<400> SEQUENCE: 1

His Pro Leu Gly Ser Pro Gly Ser Ala Ser Asp Leu Glu Thr Ser Gly
 1               5                  10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60
```

```
Arg Lys Met Val Leu Tyr Thr Leu Arg Ala Pro Arg Ser Pro Lys Met
65              70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105
```

POLYCLONAL-MONOCLONAL ELISA ASSAY FOR DETECTING N-TERMINUS PROBNP

CROSS REFERENCE TO RELATED APPLICATIONS

This application is a continuation of U.S. patent application Ser. No. 10/359,051, filed on Feb. 4, 2003 now abandoned, which is a continuation of U.S. patent application Ser. No. 10/300,733, filed on Nov. 18, 2002 now abandoned, the contents of which are herein incorporated by reference.

FIELD OF THE INVENTION

This invention relates to an NT-proBNP protein ELISA assay procedure and test kit which is a specific and sensitive in vitro assay for measuring the concentration of NT-proBNP in bodily fluids, particularly human plasma. The invention particularly relates to an NT-proBNP protein ELISA assay having a particularly high diagnostic specificity, whereby the assay is particularly designed to be predictive of mortality as a result of congestive heart failure.

BACKGROUND OF THE INVENTION

B-type natriuretic peptide (Brain natriuretic peptide, BNP) belongs to the family of structurally similar, but genetically distinct natriuretic peptides (NPs) first described by de Bold et al. (de Bold A J. Heart atria granularity: effects of changes in water-electrolyte balance. Proc Soc Exp Biol Med 1979; 161:508-511; de Bold A J, Borenstein H B, Veress A T and Sonnenberg H. A rapid and potent natriuretic response to intravenous injection of atrial myocardial extracts in rats. Life Sci 1981; 28:89-94).

The NPs possess potent diuretic, natriuretic and vasodilatory properties and have been reported as valuable diagnostic and prognostic markers in cardiovascular disease, particularly for patients in New York Heart Association (NYHA) classes I-IV congestive heart failure (CHF)(Boomsma F and van den Meiracker A H. Plasma A- and B-type natriuretic peptides: physiology, methodology and clinical use. Cardiovasc Res 2001; 51:442-449).

The BNP gene encodes for a 108 amino acid residue precursor molecule, proBNP (Sequence ID No. 1). Prior to secretion by cardiomyocytes, cleavage of this prohormone results in the generation of bioactive BNP from the COOH terminus. In 1995, Hunt et al. (Hunt P J, Yandle T G, Nicholls M G, Richards A M and Espiner E A. The Aminoterminal Portion Of Probrain Natriuretic Peptide (Probnp) Circulates In Human Plasma. Biochem Biophys Res Commun 1995; 14:1175-1183; Hunt P J, Richards A M, Nicholls M G, Yandle T G, Doughty R N and Espiner E A. Immunoreactive Amino-Terminal Pro-Brain Natriuretic Peptide (NT-PROBNP): A New Marker Of Cardiac Impairment. Clin Endocrinol 1997; 47:287-296) demonstrated that fragments corresponding to the N-terminal portion of the cleaved prohormone, NT-proBNP, also circulated in plasma, and like BNP, were a potentially important, and possibly more discerning, marker of ventricular dysfunction.

Many studies have demonstrated the clinical utility of measuring plasma concentrations of NPs, including NT-proBNP. NPs have been suggested as the biomarkers of choice for diagnosis and risk stratification of patients with heart failure (Clerico A, Del Ry S and Giannessi D. Measurement Of Cardiac Natriuretic Hormones (Atrial Natriuretic Peptide, Brain Natriuretic Peptide, And Related Peptides) In Clinical Practice: The Need For A New Generation Of Immunoassay Methods. Clin Chem 2000; 46:1529-1534: Mair J, Hammerer-Lercher A and Puschendorf B. The Impact Of Cardiac Natriuretic Peptide Determination On The Diagnosis And Management Of Heart Failure. Clin Chem Lab Med 2001; 39:571-588; Sagnella G A. Measurement And Importance Of Plasma Brian Natriuretic Peptide And Related Peptides. Ann Clin Biochem 2001; 38:83-93; Selvais P L, Donckier J E, Robert A, Laloux O, van Linden F, Ahn S, Ketelslegers J M and Rousseau M F. Cardiac Natriuretic Peptides For Diagnosis And Risk Stratification In Heart Failure: Influences Of Left Ventricular Dysfunction And Coronary Artery Disease On Cardiac Hormonal Activation. Eur J Clin Invest 1998; 28:636-642; McDonagh T A, Cunningham A D, Morrison C E, McMurray J J, Ford I, Morton J J and Dargie H J. Left Ventricular Dysfunction, Natriuretic Peptides, And Mortality In Urban Population. Heart 2001; 86:21-26). Several studies have shown the utility of using NP measurements to identify patients with left ventricular dysfunction, even amongst patients who are asymptomatic (i.e. NYHA class I) and it has been suggested that NP measurements as a screening tool may help effectively target patients within high risk heart failure groups (e.g. coronary artery disease, hypertension, diabetes, aged) who will require follow-up assessment and treatment (Hughes D, Talwar S, Squire I B, Davies J E and Ng L L. An Immunoluminometric Assay For N-Terminal Pro-Brain Natriuretic Peptide: Development Of A Test For Left Ventricular Dysfunction. Clin Sci 1999; 96:373-80; Omland T, Aakvaag A, Vik-Mo H. Plasma Cardiac Natriuretic Peptide Determination As A Screening Test For The Detection Of Patients With Mild Left Ventricular Impairment. Heart 1996; 76:232-237; McDonagh T A, Robb S D, Murdoch D R, Morton J J, Ford I, Morrison C E, et al. Biochemical Detection Of Left-Ventricular Systolic Dysfunction. Lancet 1998; 351:9-13; Schulz H, Langvik T A, Lund Sagen E, Smith J, Ahmadi N and Hall C. Radioimmunoassay For N-Terminal Probrain Natriuretic Peptide In Human Plasma. Scand J Clin Lab Invest 2001; 61:33-42; Talwar S, Squire I B, Davies J E, Barnett D B and Ng L L. Plasma N-Terminal Pro-Brain Natriuretic Peptide And The ECG In The Assessment Of Left-Ventricular Systolic Dysfunction In A High Risk Population. Eur Heart J 1999; 20:1736-1744; Hystad M E, Geiran O R, Attramadal H. Spurkland A, Vege A, Simonsen S and Hall C. Regional Cardiac Expression And Concentration Of Natriuretic Peptides In Patients With Severe Chronic Heart Failure. Acta Physiol Scand 2001; 171:395-403; Hobbs F D R, Davis R C, Roalfe A K, Hare R, Davies M K and Kenkre J E. Reliability Of N-Terminal Pro-Brain Natriuretic Peptide Assay In Diagnosis Of Heart Failure: Cohort Study In Representative And High Risk Community Populations. BMJ 2002; 324:1498). NPs have been shown to have good prognostic value with regards to both morbidity and mortality in heart failure. Several studies have also demonstrated the utility of NP measurements in the prediction of left ventricular dysfunction and survival following acute myocardial infarction (Richards A M, Nicholls M G, Yandle T G, Frampton C, Espiner E A, Turner J G, et al. Plasma N-Terminal Pro-Brain Natriuretic Peptide And Adrenomedullin. New Neurohormonal Predictors Of Left Ventricular Function And Prognosis After Myocardial Infarction. Circulation 1998; 97:1921-1929; Luchner A, Hengstenberg C, Lowel H, Trawinski J, Baumann M, Riegger G A J, et al. N-Terminal Pro-Brain Natriuretic Peptide After Myocardial Infarction. A Marker Of Cardio-Renal Function. Hypertension 2002; 39:99-104; Campbell D J, Munir V, Hennessy O F and Dent A W. Plasma Amino-Terminal Pro-Brain Natriuretic Peptide Levels In Subjects Presenting To The Emergency Department With Suspected Acute Coronary Syndrome: Possible Role In Selecting Patients For Follow Up? Intern Med J 2001; 31:211-219; Nilsson J C, Groenning B A, Nielsen G, Fritz-Hansen T, Trawinski J, Hildebrandt P R, et al. Left Ventricular Remodeling In The First Year After Acute Myocardial Infarction And The Predictive Value Of N-Terminal Pro Brain Natriuretic Peptide. Am Heart J 2002; 143:696-702). Monitoring NP levels may also provide guidance in tailoring therapies to meet the required intensity of the individual patient and in monitoring therapeutic efficacy (Richards A M, Doughty R, Nicholls G, MacMahon S, Sharpe N, Murphy J, et al. Plasma N-Terminal Pro-Brain Natriuretic Peptide And Adrenomedullin. Prognostic Utility And Prediction Of Benefit From Carvedilol In Chronic Ischemic Left Ventricular Dysfunction. J Am Coll Cardiol 2001; 37:1781-1787; Troughton R W, Frampton C M, Yandle T G, Espiner E A, Nicholls M G and Richards A M. Treatment Of Heart Failure Guided By Plasma Aminoterminal Brain Natriuretic Peptide (N-BNP) Concentrations. Lancet 2000; 355:1126-30).

PRIOR ART

WO 93/24531 (U.S. Pat. No. 5,786,163) to Hall describes an immunological method of identifying N-terminal proBNP and the antibodies used for it. To obtain these antibodies single synthetically produced peptides from the sequence of N-terminal proBNP are used. The production of antibodies by means of peptide immunization is possible in principle but the affinity regarding the whole molecule generally is too low to reach the necessary sensitivity in a test procedure. In addition, there is a danger that when using peptides the antibodies obtained can, for example, identify the C-terminus of the peptide and can therefore only bind to this fragment of the whole molecule, thus resulting in antibodies which generally cannot bind to the whole molecule, or can do so to only a limited extent. In WO 93/24531 an antibody against one single peptide derived from the N-terminal proBNP is produced. It is shown that the antibodies produced bind to the immunization peptide (amino acids 47-64) in the competitive test format. It is however not shown that the antibodies are able to bind to native N-terminal proBNP as a whole molecule in a sample. Additionally, the sandwich test described in WO 93/24531 in a sample cannot be performed as described since there was no appropriate standard material and no antibodies against two different epitopes. Additionally, the competitive test performed in PCT 93/24531, where the peptide 47-64 competes in a labelled form as a tracer with a sample or the unlabelled peptide standard 47-64 to bind to polyclonal antibodies from rabbit serum, suffers from the fact that only a very moderate competition is reached after 48 hours of incubation from which only a low detection limit of approx. 250 fmol/ml can be derived. This is neither sufficient for the differentiation of healthy individuals and patients suffering from heart failure nor for a differentiated classification of patient samples into the severity degrees of heart failure. In addition, the long incubation times of the competitive test are not acceptable for routine measurements of the samples in automated laboratories.

Hunt et al. (Clinical Endocrinology 47 (1997), 287-296) also describes a competitive test for the detection of N-terminal proBNP. For this a complex extraction of the plasma sample is necessary before the measurement; this may lead to the destruction of the analyte and error measurements. The antiserum used is produced analogously to WO 93/24531 by immunization with a synthetic peptide-Hunt et al. produces the antiserum by immunization with the N-terminal proBNP amino acids 1-13 and the peptide of amino acids 1-21 is used as a standard. For this test long incubation times are necessary too. After an incubation of 24 hours a lower detection limit of 1.3 fmol/ml is reached.

WO 00/45176, Method of Identifying N-Terminal proBNP, Karl et al., discloses monoclonal and polyclonal antibodies isolated via the use of a recombinant NT-proBNP immunogen. The reference suggests the formation of an assay using the disclosed antibodies as being specific for NT-proBNP in bodily fluids. As will be more fully described, a comparison of the area under the curve (AUC) of a plot of the Receiver Operated Characteristics (ROC) for this assay versus the assay of the instant invention indicates that the instant invention demonstrates superior diagnostic performance.

WO 00/35951, Natriuretic Peptide Fragments, is directed toward an assay for NT-proBNP utilizing two antibodies directed toward differing epitopes of the NT-proBNP sequence. This assay suffers from similar deficiencies as that of Hall (U.S. Pat. No. 5,786,163) in that the antibodies are raised against synthetic peptide fragments as the immunogen.

SUMMARY OF THE INVENTION

The instantly disclosed NT-proBNP protein ELISA assay and test kit is a specific and sensitive in vitro assay that is capable of measuring the concentration of NT-proBNP in a variety of bodily fluids, non-limiting examples of which are blood, serum, plasma, urine and the like. The following examples and descriptions will exemplify the use of the assay in human plasma.

As used herein, the term "antibody or antibodies" includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library.

The NT-proBNP ELISA assay test employs the sandwich ELISA technique to measure circulating NT-proBNP in human plasma.

In order to obtain antibodies with specific binding properties for targeted amino acid sequences within human proBNP, recombinant human proBNP (or rhproBNP) was expressed and purified for use as an immunogen. Polyclonal antibodies (PAb) specific for amino acid sequences within proBNP (1-25, 26-51, 52-76 or 77-108) of Sequence ID No. 1 were subsequently purified from goat serum by sequential affinity purification In order to obtain material for use in calibration of a quantitative method for measurement of human NT-proBNP, recombinant human NT-proBNP (or rhNT-proBNP) was expressed and purified. Monoclonals were produced from supernatants for use in an NT-proBNP ELISA in pairing with the instantly described Goat Polyclonal Antibodies. The monoclonals were biotinylated and used as a detector antibody to bind to the NT-proBNP protein bound to anti-NT-proBNP capture antibody, thus forming a sandwich.

Accordingly, it is an objective of the instant invention to provide goat polyclonal antibodies raised against recombinant human proBNP, which antibodies are specifically selected to exhibit a specific affinity for targeted amino acid sequences within human proBNP.

It is a further objective of the instant invention to provide a quantitative method for measurement of human NT-proBNP, whereby a diagnostic/screening tool for accurately predicting mortality in congestive heart failure patients may be determined.

It is yet an additional objective of the instant invention to provide monoclonal antibodies useful in providing a particularly sensitive and specific in vitro diagnostic assay when combined with the previously selected goat polyclonal antibodies.

It is still an additional objective of the instant invention to provide an ELISA Test Kit for the purpose of carrying out the above-outlined diagnostic/screening procedure to determine levels of NT-proBNP.

BRIEF DESCRIPTION OF THE FIGURES

FIG. 1 illustrates the method of selection of NT-proBNP and target peptides starting from a pre-proBNP precursor protein;

FIG. 2 is an ROC curve for the goat polyclonal/6G11 monoclonal assay;

FIG. 3 is a box-plot of NT-proBNP levels in NYHA Class III and IV versus controls;

FIG. 4 is a box-plot of NT-proBNP levels in control subjects, stratified by age;

DETAILED DESCRIPTION OF THE INVENTION

Figure 5:
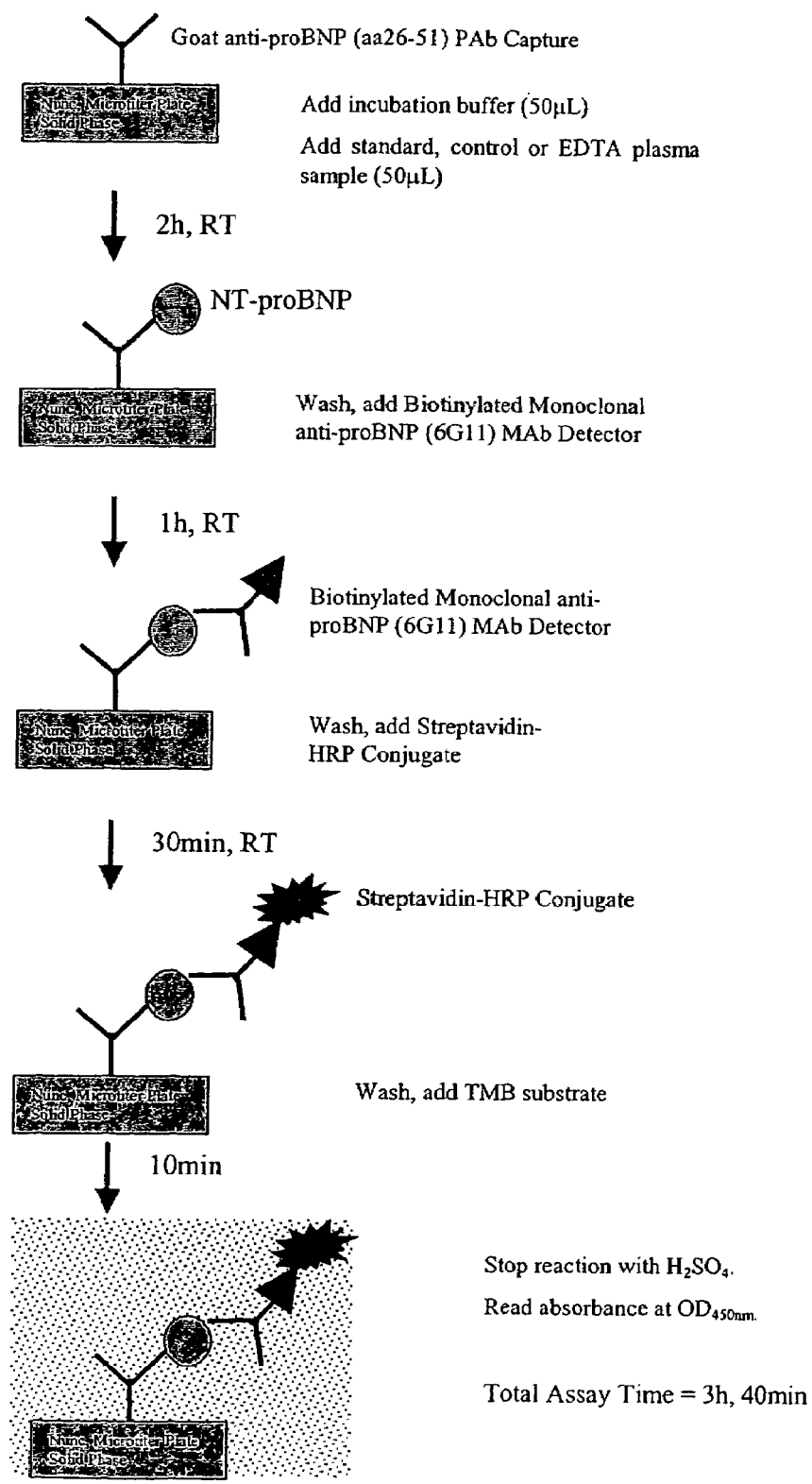
FIG. 5 outlines the ELISA procedure for utilizing the goat polyclonal/6G11 monoclonal assay of the instant invention.

The NT-proBNP ELISA assay test employs the sandwich ELISA technique to measure circulating NT-proBNP in human plasma. Microplate wells coated with goat polyclonal anti-NT-proBNP capture protein constitute the solid phase. Test subject plasma, standards and controls are added to the coated wells and incubated with incubation buffer. No sample extraction step is required. If NT-proBNP protein is present in the test sample, it will be captured by NT-proBNP specific antibody coated on the wells. After incubation and washing, a monoclonal anti-NT-proBNP detector antibody is added to the wells. The detector antibody binds to the NT-proBNP protein, or immunogenic fragments thereof, e.g. polypeptide fragments which are recognized by said antibody, bound to anti-NT-proBNP capture antibody, thus forming a sandwich. After incubation and washing, a polyclonal donkey anti-mouse IgG labeled with horseradish peroxidase (HRP) is added to the wells. Following incubation and washing, an enzyme substrate is added to the wells and incubated. An acidic solution is then added in order to stop the enzymatic reaction. The degree of enzymatic activity of immobilized HRP is determined by measuring the optical density of the oxidized enzymatic product in the wells at 450 nm. The absorbance at 450 nm is proportional to the amount of NT-proBNP in the test subject sample. A set of NT-proBNP protein standards is used to generate a standard curve of absorbance versus NT-proBNP concentration from which the NT-proBNP concentrations in test specimens and controls can be calculated. It is understood that detection of the immunoreaction may be accomplished via direct or indirect methods which are well-known in the art.

In order to obtain antibodies with specific binding properties for targeted amino acid sequences within human proBNP, recombinant human proBNP (or rhproBNP) was expressed and purified for use as an immunogen. ProBNP-pUC9 plasmid construct was obtained from Dr. Adolfo J. de Bold (Ottawa Heart Institute). The full-length rhproBNP open reading frame (ORF) was obtained by polymerase chain reaction (PCR) and subcloning into pET32c (NcoI/XhoI). The pET32c vector was modified by removing 81 nucleotides so that the final fusion protein would not contain the S-tag and enterokinase sites. The sequence at the N-terminus of the rhproBNP ORF consisted of thioredoxin and poly-histidine tags and a thrombin cleavage site. There was no extra sequence at the C-terminus. The protein was expressed in Escherichia coli BL21 (DE3) cells and the crude cellular extract was prepared in non-denaturing conditions. The subsequent affinity purification was completed by Ni-NTA chromatography following the supplier's recommendations. Prior to injections, endotoxin levels in the rhproBNP solutions were lowered to acceptable levels using a Detoxigel® endotoxin-removing resin following the supplier's recommendations.

Polyclonal Antibody Production and Purification

Goats (La Mancha or Toggenburg breed) were immunized with purified recombinant human full-length proBNP (rhproBNP). A primary intramuscular injection at multiple sites of 500 ug purified rhproBNP emulsified in Complete Freund's Adjuvant was administered, followed by bi-weekly 250 ug intramuscular injections at multiple sites of the purified rhproBNP emulsified in Freund's incomplete adjuvant. The titer of immunized goats was monitored routinely by screening serum using a half-sandwich ELISA technique.

Polyclonal antibodies (PAb) specific for amino acid sequences within proBNP (1-25, 26-51, 52-76 or 77-108) of Sequence ID No. 1 were subsequently purified from goat serum by sequential affinity purification using cyanogen bromide activated sepharose-4B (Pharmacia) coupled, according to the supplier's recommendations, to the following proteins or peptide sequences:

human IgG (Jackson ImmunoResearch)
mouse IgG (Jackson ImmunoResearch)
proBNP amino acid sequence #1-25 of Sequence ID No. 1(H P L G S P G S A S D L E T S G L Q E Q R N H L Q) coupled to Keyhole Limpet Haemocyanin (ADI Inc.) OR
proBNP amino acid sequence #26-51 of Sequence ID No. 1 (G K L S E L Q V E Q T S L E P L Q E S P R P T G V W) coupled to Keyhole Limpet Haemocyanin (ADI Inc.) OR
proBNP amino acid sequence #52-76 of Sequence ID No. 1 (K S R E V A T E G I R G H R K M V L Y T L R A P R) coupled to Keyhole Limpet Haemocyanin (ADI Inc.) OR
proBNP amino acid sequence #77-108 of Sequence ID No. 1 (BNP-32, S P K M V Q G S G C F G R K M D R I S S S S G L G C K V L R R H) coupled to Keyhole Limpet Haemocyanin (ADI Inc.)

The purified polyclonal antibodies were dialyzed against 20 mM PBS, pH 7.4, concentrated by ultrafiltration and stored at −20° C.

Expression of Recombinant Human NT-proBNP

In order to obtain material for use in calibration of a quantitative method for measurement of human NT-proBNP, recombinant human NT-proBNP (or rhNT-proBNP) was expressed and purified. A proBNP-pUC9 plasmid construct was obtained from Dr. Adolfo J. de Bold (Ottawa Heart Institute). The rhNT-proBNP ORF was obtained by PCR and subcloning into pET32c (NcoI/XhoI). The sequence at the N-terminus of the rhNT-proBNP ORF consisted of thioredoxin, poly-histidine, and S-tag tags, as well as thrombin and enterokinase cleavage sites. There was no extra sequence at the C-terminus. The protein was expressed in Escherichia coli BL21 (DE3) cells and the crude cellular extract was prepared in non-denaturing conditions. The subsequent affinity purification was completed by Ni-NTA chromatography following the supplier's recommendations.

Screening of Monoclonal Antibodies

Monoclonal antibodies, secreted by hybridoma cell lines herein designated as 6G11-F11-D12 and as 1C3-E11-H9 for use in a method of immunoassay, wherein said antibodies are specific to the polypeptide consisting of amino acids 1-25 of human N-terminal brain natriuretic factor BNP (1-25), were obtained from Dr. Adolfo J. De Bold. These monoclonals were produced from supernatants for use in an NT-proBNP ELISA in pairing with the instantly described Goat Polyclonal Antibodies, and are designated 6G11 and 1C3 respectively. These clones are the subject of U.S. Ser. No. 10/299,606 filed on even date herewith, the contents of which are herein incorporated by reference, and were deposited, in accordance with the Budapest Treaty, with the American Type Culture Collection, 10801 University Blvd., Manassas, Va. 20110-2209 on Dec. 5, 2002 under Accession Numbers PTA-4844 and PTA-4845 respectively. In accordance with 37 CFR 1.808, the depositors assure that all restrictions imposed on the availability to the public of the deposited materials will be irrevocably removed upon the granting of a patent. The depositors additionally assure that the deposited materials will be replaced if viable samples cannot be dispensed by the depository.

Screening was conducted for:

i) Potential Capture MAb(s) with Goat PAb as Detector

Confluent hybridoma culture supernatants were added to 96-well microtiter plates (NUNC, MaxiSorp, GIBCO BRL) coated with donkey anti-mouse IgG$_{(H+L)}$ immunoglobulins (Jackson ImmunoResearch) at 2 µg/ml in 100 mM carbonate buffer, pH 9.6. Excess binding sites were blocked with bovine serum albumin (BSA) in PBS, pH 7.4. After washing the plate with wash buffer (PBS containing 0.05% (v/v) Tween 20), 50 µL of each culture supernatant containing monoclonal antibody was incubated on the plate. Following 1 hour incubation at 37° C. in a $CO_2$ incubator, the plate was washed with wash buffer. Recombinant human proBNP (Syn-X Pharma) was then added to the plate at concentrations of 3 ng/ml or 0 ng/ml, and the plate incubated for 2 hours at room temperature (RT) on a shaker. After washing the plate, biotinylated goat polyclonal antibodies affinity purified against proBNP amino acid peptide sequences 1-25, 26-51 or 52-76 (Syn-X Pharma), diluted appropriately in PBS with 0.5% (w/v) BSA, were added to the appropriate wells. Goat polyclonal antibodies were biotinylated using a Biotin Labeling Kit from Roche following the manufacturer's recommendations. After 1 hour incubation at RT on a shaker, the plate was washed and HRP-conjugated streptavidin (Jackson ImmunoResearch) at a dilution of 1/5000 was added and incubated for 1 hour at RT on a shaker. Following washing, TMB substrate solution (Moss) was added and after 8 minutes incubation at RT in the dark, the reaction was stopped with 1 N $H_2SO_4$ and optical density read at 450$_{nm}$. Clones were selected for ascites production based on ability to pair with the respective goat polyclonal antibody to produce a specific high intensity signal in wells containing proBNP antigen, and minimal signal in wells containing no proBNP antigen.

ii) Potential Detector MAb(s) with Goat PAb as Capture 96-well microtiter plates were coated with goat polyclonal antibodies affinity purified against proBNP amino acid peptide sequences 1-25, 26-51, or 52-76 (Syn-X Pharma) at 1 µg/ml in 100 mM carbonate buffer, pH 9.6. Excess binding sites were blocked as for method (i). After washing with wash buffer, recombinant human proBNP (Syn-X Pharma) was added to the wells at concentrations of 3 ng/ml or 0 ng/ml and the plate incubated for 2 hours at RT on a shaker. Following washing, confluent hybridoma culture supernatants containing monoclonal antibodies were added (50 µL per well) and the plates incubated for 1 hour at 37° C. in a $CO_2$ incubator. After another wash step, HRP conjugated donkey anti-mouse IgG$_{(H+L)}$ (Jackson ImmunoResearch) at a dilution of 1/5000 was added to the plate and incubated for 1 hour at RT on a shaker. TMB substrate was added, after washing, and the plates developed as for method (i). Clones were selected for ascites production based on ability to pair with the respective goat polyclonal antibody to produce a specific high intensity signal in wells containing proBNP antigen, and minimal signal in wells without antigen.

Final Selection of 6G11 Monoclonal Antibody

Following production of the selected monoclonal antibodies by ascites, and subsequent purification by Protein G (Pharmacia) using known procedures, the purified antibodies were retested as described above for screening of hybridoma supernatants, but for the fact that the purified monoclonal antibodies were appropriately diluted in 100 mM carbonate buffer, pH 9.6 and coated directly onto the plate for screening as captures, or appropriately diluted in PBS containing 0.5% (w/v) BSA for screening as detectors.

Optimal ELISA specificity and sensitivity for recombinant human proBNP and recombinant human NT-proBNP were obtained using the combination of goat polyclonal antibody affinity purified against proBNP amino acid peptide sequence 26-51 as capture with MAb clone designate 6G11 as detector. Now referring to FIG. 5, the procedure for carrying out the ELISA assay of the instant invention is set forth.

Subsequent analysis of the data derived from human plasma samples tested in accordance with these procedures have demonstrated the utility of this antibody combination for yielding excellent sensitivity and specificity when measuring NT-proBNP levels in apparently healthy individuals versus heart failure patients.

In accordance with this invention, an ELISA Test Kit is provided for the purpose of carrying out the above-outlined procedure.

Reagents Supplied

Anti-NT-proBNP Protein Coated Microtitration Strips

One stripholder containing 96 microtitration wells coated with goat polyclonal anti-NT-proBNP antibody. Store at 2-8° C., in the pouch with desiccant, until expiry.

NT-proBNP Protein Standards

Six vials, each containing one of the following standards: 0, 50, 150, 375, 1500, and 3000 pg/ml of NT-proBNP, are provided. Each vial contains 0.5 ml, except for the 0 pg/ml standard which contains 1.0 ml. The extra volume allows for diluting samples that have values greater than 3000 pg/ml, if retesting is desired. Store at −70±10° C. Kept at this temperature, the standards are stable for at least 3 cycles of freeze/thaw and up to 6 months.

NT-proBNP Protein Controls

Two vials, 0.5 ml each, containing NT-proBNP controls at low and high protein concentration. Store at −70±10° C. Kept at this temperature, the controls are stable for at least 3 cycles of freeze/thaw and up to 6 months.

Incubation Buffer

One vial containing 10 ml of incubation buffer. Store at 2-8° C. until expiry.

Detector Antibody

One vial containing 10 ml of monoclonal anti-NT-proBNP antibody. Store at 2-8° C. until expiry.

Horseradish Peroxidase (HRP) Conjugate

One vial containing 10 ml of donkey anti-mouse immunoglobulins labeled with horseradish peroxidase. Store at 2-8° C. until expiry.

Chromogen Solution

One vial containing 10 ml of 3,3',5,5'-tetramethylbenzidine (TMB) substrate solution. Store at 2-8° C. until expiry.

Wash Concentrate

One bottle containing 60 ml phosphate buffered saline with nonionic detergent. Dilute contents 25 fold with deionized water before use. Store at 2-8° C.

Stopping Solution

One bottle containing 10 ml 1N sulfuric acid. Store at 2-8° C.

Assay Procedure

In carrying out the assay, the time between addition of samples, standards, and controls to the first well and the last well should not exceed 10 minutes. For large series of samples, run the ELISA in small batches to accommodate this time frame.

Mark the microplate wells to be used.

Add 50 µl of the incubation buffer to each well using a semi-automatic pipette.

Using a precision micropipette, add 50 µl of each test sample, NT-proBNP standard, or NT-proBNP control to the appropriate microwell. In order to ensure standard curve consistency, the following order of addition to the plate is recommended:

Test samples
NT-proBNP standards
NT-proBNP controls

It is recommended that NT-proBNP standards and controls be assayed in duplicate.

Cover microwells using an adhesive plate cover and incubate for 2 hours on an orbital microplate shaker at room temperature.

Aspirate and wash each microwell three times with the wash solution using an appropriate microplate washer. Blot dry by inverting the plate on absorbent material.

Since incomplete washing adversely affects assay precision, the use of an automatic microplate washer is highly recommended. Alternatively, if an automatic microplate washer is not available, washing can be accomplished manually by repeatedly aspirating microwell contents and refilling each microwell with 340 µl of wash solution, three times.

Add 100 µl of detector antibody solution to each well using a semi-automatic pipette.

Incubate the wells for 1 hour on an orbital microplate shaker at room temperature.

Aspirate and wash microwells three times with the wash solution using an appropriate microplate washer. Blot dry by inverting the plate on absorbent material.

Add 100 µl of HRP conjugate solution to each well using a semi-automatic pipette.

Cover microwells using an adhesive plate cover and incubate for 30 minutes on an orbital microplate shaker at room temperature.

Aspirate and wash microwells three times with wash solution. Blot dry by inverting the plate on absorbent material.

Add 100 µl of the TMB solution to each well using a semi-automatic pipette.

Incubate the wells in the dark for 5 minutes at room temperature. Avoid exposure to direct sunlight.

Add 100 µl of stopping solution (1N sulfuric acid) to each well using a semi-automatic pipette.

Measure the absorbance of the solution in the microwells using a microplate reader at 450 nm.

Calculation of Results

Calculate the mean absorbance for each well containing standard, control or test subject plasma.

Plot the mean absorbance reading for each of the standards along the y-axis (quadratic) versus the NT-proBNP concentration, in pg/ml, along the x-axis (linear).

Draw the best fitting standard curve through the mean of the duplicate points.

Determine the NT-proBNP concentrations of the test subjects' plasma and controls by interpolating from the standard curve.

Subject plasma specimens reading lower than the lowest standard should be reported as such.

Alternatively, a computer program may be used for handling ELISA type data to evaluate the NT-proBNP concentrations in test subjects' plasma and controls.

The following data represent an example dose response curve using this assay:

| Standard Dose (pg/ml) | Mean OD 450 nm |
| --- | --- |
| 0 | 0.046 |
| 50 | 0.095 |
| 150 | 0.178 |
| 375 | 0.347 |
| 1500 | 1.161 |
| 3000 | 1.781 |

Note: These values should not be used in lieu of a standard curve, which should be prepared at the time of assay.

Performance Characteristics

In order to insure quality control standards, two controls designated—low and high—provided in the kit must be analyzed in each assay. It is recommended that each laboratory use additional controls for validation of each assay run.

Summary of NT-proBNP Clinical Data for the Goat Polyclonal-6G11 Monoclonal Elisa Assay Data is available from 209 subjects diagnosed with congestive heart failure (NYHA Class III and Class IV) and 101 healthy normal control subjects. The receiver operating characteristic (ROC) curve is displayed in FIG. 2; an area under the curve (AUC) of 0.974 was obtained, with a corresponding standard error (s.e.) of 0.008. FIG. 3 displays boxplots of NT-proBNP levels in the control subjects and the heart failure subjects; at a cutoff level of 165 pg/mL, the diagnostic sensitivity with respect to the heart failure subjects was 90.4% (with 189 out of 209 such subjects with NT-proBNP levels above the cutoff) and the diagnostic specificity with respect to the control subjects was 94.1% (with 95 out of 101 such subjects with NT-proBNP levels below the cutoff).

Comparison with Other NT-proBNP and BNP Assays

In the product insert for the Biosite Triage BNP test (Triage© B-Type Natriuretic Peptide (BNP) Test, Product insert, Biosite Diagnostics, Inc., 2001), a ROC curve analysis on clinical data obtained from 804 heart failure subjects and 1286 control subjects revealed an AUC of 0.955 (standard error=0.0053). Comparing this AUC with that of the instantly disclosed NT-proBNP assay, following the procedure of Hanley and McNeil (Hanley J A and McNeil B J (1982). "The meaning and use of the area under a receiver operating characteristic (ROC) curve." *Radiology* 143 29-36), one finds that the instantly disclosed NT-proBNP assay has a significantly higher AUC ($p<0.001$), indicative of superior diagnostic performance.

Fischer et al. (Fischer Y, Filzmaier K, Stiegler H, Graf J, Fuhs S, Franke A, Janssens U and Gressner A M (2001). "Evaluation of a New, Rapid Bedside Test for Quantitative Determination of B-Type Natriuretic Peptide." *Clinical Chemistry* 47 591-594.) gave performance data comparing the Triage BNP test to an NT-proBNP EIA assay from Roche Diagnostics with respect to 93 subjects with underlying cardiac disease and suspected heart failure. In distinguishing subjects with decreased ventricular function from those with preserved ventricular function, an AUC of 0.91 (±0.033 s.e.) was obtained for the Triage BNP test, and an AUC of 0.86 (±0.040 s.e.) was obtained for the Roche NT-proBNP assay. Given a reported correlation between the two neurohormone measurements of r=0.947, and following the method of Hanley and McNeil (Hanley J A and McNeil B J (1983), "A method of comparing the areas under Receiver Operating Characteristic curves derived from the same cases." *Radiology* 148 839-843) for comparing AUC's derived from the same set of cases, one finds that the Triage BNP test has a significantly higher AUC than that of the Roche NT-proBNP assay (p=0.005).

Hammerer-Lercher et al. (Hammerer-Lercher A, Neubauer E, Müller S, Pachinger O, Puschendorf B and Mair J (2001). "Head-to-head comparison of N-terminal pro-brain natriuretic peptide, brain natriuretic peptide and N-terminal pro-atrial natriuretic peptide in diagnosing left ventricular dysfunction." *Clinica Chimica Acta* 310 193-197) compared the Shionogi IMRA BNP assay to the Biomedica EIA NT-proBNP assay with respect to the same population of 57 patients with stable chronic heart failure. In distinguishing subjects with decreased ventricular function from those with preserved ventricular function, an AUC of 0.75 (±0.06 s.e.) was obtained for the BNP assay, and an AUC of 0.67 (±0.07 s.e.) was obtained for the Biomedica NT-proBNP assay. Following the method of Hanley and McNeil (Hanley J A and McNeil B J (1983). "A method of comparing the areas under Receiver Operating Characteristic curves derived from the same cases." *Radiology* 148 839-843), one finds that the Shionogi BNP assay has a significantly higher AUC than that of the Biomedica NT-proBNP assay (p=0.009).

Luchner et al. (Luchner A, Hengstenberg C, Löwel H, Trawinski J, Baumann M, Riegger G, Schunkert H and Holmer S (2002). "N-Terminal Pro-Brain Natriuretic Peptide After Myocardial Infarction." *Hypertension* 39 99-104) conducted a large clinical study involving 594 myocardial infarction subjects and 449 healthy controls, in order to determine the ability of the Roche EIA NT-proBNP assay to predict decreased ventricular function in these subjects. The authors quoted an AUC of 0.77 (±0.057 s.e.) with respect to NT-proBNP in separating subjects with a left ventricular ejection fraction of less than 35% from those with a higher ejection fraction. This AUC is significantly lower than that quoted above for the instantly disclosed NT-proBNP assay (p=0.0001).

Thus, on the basis of quantifying the variously available assays for determining the presence of NT-proBNp based upon an area under the curve analysis, the instant assay would be expected to exhibit superior diagnostic performance.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for identifying a patient with congestive heart failure of New York Heart Association (NYHA) classes III or IV by determining concentration of N-terminal pro-brain natriuretic peptide (NT-proBNP) in a bodily fluid sample, comprising:
   (a) obtaining isolated polyclonal antibodies specific for amino acid residues 26-51 of SEQ ID No: 1 and attaching said isolated polyclonal antibodies to a solid support;
   (b) obtaining a sample of a bodily fluid from said patient wherein said sample is suspected of containing immunogenic fragments of NT-proBNP;
   (c) adding said sample to said isolated polyclonal antibodies of step (a) wherein said immunogenic fragments of NT-proBNP contained in said sample are captured by said isolated polyclonal antibodies;
   (d) providing monoclonal antibodies produced by a hybridoma cell line designated as 6G11-F11-D12 and deposited with the American Type Culture Collection (ATCC) as Accession Number PTA-4844, wherein said monoclonal antibodies are specific for amino acid residues 1-25 of SEQ ID NO:1;
   (e) labeling said monoclonal antibodies with a detector;
   (f) adding said monoclonal antibodies of step (e) to said immunogenic fragments of NT-proBNP captured in step (c) wherein said monoclonal antibodies of step (e) bind to said immunogenic fragments of NT-proBNP captured in step (c);
   (g) adding a reporter that reacts with said detector to form a reaction product; and
   (h) measuring said reaction product to determine concentration of NT-proBNP in said sample; and
   (i) determining if said concentration of NT-proBNP in said sample is elevated above a selected cut-off concentration indicative of concentration of NT-proBNP in a sample of said bodily fluid from a normal human; wherein said elevated concentration identifies that the patient has congestive heart failure of NYHA classes III or IV.

2. The process of claim 1 wherein said bodily fluid is plasma.

3. The process of claim 1 wherein the detector is biotin.

4. The process of claim 3 wherein the reporter is peroxidase-labeled streptavidin.

* * * * *